United States Patent [19]

Tzur

[11] Patent Number: 5,686,516
[45] Date of Patent: Nov. 11, 1997

[54] COMPOSITIONS FOR DISPOSABLE BIO-MEDICAL ELECTRODES

[75] Inventor: Yoel Tzur, Rishon-Letzion, Israel

[73] Assignee: S.L.P. Scientific Laboratory Products, Ltd., Technion, Israel

[21] Appl. No.: 490,675

[22] Filed: Jun. 15, 1995

[30] Foreign Application Priority Data

Jul. 24, 1994 [IL] Israel .......................................... 110419

[51] Int. Cl.$^6$ ............................... C08K 5/04; C08K 3/10
[52] U.S. Cl. .................... 524/394; 524/403; 524/436; 524/437; 524/427; 524/492; 524/493; 524/495; 428/356
[58] Field of Search .............................. 524/394, 403, 524/436, 437, 447, 492, 493, 495; 428/356

[56] References Cited

U.S. PATENT DOCUMENTS

| | | |
|---|---|---|
| 4,215,696 | 8/1980 | Bremer et al. .......................... 128/641 |
| 4,588,762 | 5/1986 | Mruk et al. . |
| 4,938,860 | 7/1990 | Wogoman ............................... 204/403 |

*Primary Examiner*—Helen Lee
*Attorney, Agent, or Firm*—Morgan & Finnegan LLP

[57] ABSTRACT

The present invention relates to a disposable electrode for providing electrical contact with a patient's scalp or skin during routine EEG or EKG tests, as well as EEG during full sleeping period in order to record electrical brain or skin waves, which comprises an electrically conductive composition having a volume resistivity in the range of between 1000 to 1500 ohms, acting also as an adhesive to the skin or the scalp by its remoistable property. The composition comprises: (1) a partially hydrolysed polyvinyl alcohol; (2) a highly hygroscopic salt selected from an metal salt, or organic chloride salt; (3) a highly electrolytic salt, and (4) a metal powder selected from aluminium, bronze and silver. The performance of the electrode was found to be the same as those known on the market.

10 Claims, No Drawings

COMPOSITIONS FOR DISPOSABLE BIO-MEDICAL ELECTRODES

The present invention relates to novel medical electrodes. More particularly the invention relates to Biomedical electrodes for electroencephalograph (EEG) and electrocardiograph (EKG) both for routine diagnostic tests and recording during the sleeping of a person.

BACKGROUND OF THE INVENTION

As known the EEG apparatus is utilized for detecting and recording electrical brain waves for a subsequent medical diagnosis and prognosis. The EEG utilizes monitoring electrodes which are attached to the patient's scalp so as to transmit electrical waves generated by the brain to a recorder. Generally, the EEG electrode is in the form of a small disc which is conventionally attached to the scalp by means of a bentonite clay paste which is allowed to harden, or to particular adhesives useful for this purpose.

A problem which was found to decrease the effectiveness of EKG and EEG electrodes is the artifact created by the outermost dried out layer of the skin or of the scalp. This layer of skin or scalp acts as an insulator to the electrical current produced, thus preventing an accurate reading of the actual electrical current to be measured. Therefore, in case of the brain, in order to obtain an accurate reading it has been necessary to abrade the epidermus corneum to reduce the resistance of a patient's scalp to a satisfactory level. This problem occurs also with an electrocardiograph (EKG), and occurs especially in case of EEG electrodes where the extremely small voltage generated by the brain requires a very sensitive reading.

Prior art electrodes suggested to overcome the above problem were based on a combination structure including a metallic or otherwise conductive support member to which an electrical wire from the respective apparatus may be attached.

Another type of electrodes is based on the additional incorporation of an open cellular skin interface pad fixed to a conductive support member. The pad appears as a sponge material containing an electrolyte solution which should enhance conductivity across the scalp-pad interface. Thus, U.S. Pat. No, 4,5882,762 describes a conductive pressure sensitive adhesive which is directly applied as a thin layer on the surface of a dry electrode. It is claimed that in this manner, the reliability of the electrical contact between the skin and electrode is increased.

There were described also non-conductive pressure sensitive adhesive, wherein the adhesive is applied to the periphery of a dry conductive bioelectrode, such as a silver-silver chloride. The electrode is attached to the skin by application of pressure, thus creating an electric conductive contact. However, this type of electrode can not be used on scalp with hair.

One of the main defficiencies of known EEG electrodes is the fact that they are not able to maintain a constant efficient and effective electrical transmission for long periods of time without the need to add electrode paste, gel or solution. Also, these electrodes must be secured to the scalp with medical tape or other securing mediums such as particular adhesives. However, when the electrode pulls away from the scalp a partial or total interuption in the signal transmission will occur. Also the removal of these electrodes requires strong solvents, such as acetone, ether or alcohol which cause skin sensitization and raises safety problems, in addition to requiring the removal of residual adhesives.

Furthermore, preparing a patient while the patient is sleeping so that such an electrode can be applied requires about thirty minutes which is quite a long period of time, in this case.

According to a more recent improvement in the electrode art for EEG, a composite electrode using an electroconductive tape is used as the scalp interfacing medium.

The tape has a film of pressure sensitive adhesive which has been doped with electrically conductive particles such as carbon powder or silver powder. This doping creates a non-uniform electrical transmission through the adhesive. Disposable biomedical electrodes were also suggested in order to detect and record biological or physiological electrical potentials. These types of electrodes are characterised by an improved electrical contact with the skin to which they are applied. Most of these electrodes use conductive adhesive compositions as means for bonding and securing the electrode in the right place. Generally, the electrodes of the disposable type are pre-gelled, the gel being contained in a cavity filled with a porous, gel-retaining sponge-like element. The gel serves as a stabilizing factor for the adhesive by serving as a humidifier for the adhesive.

The above brief review clearly illustrates the long felt need for a novel composition for a disposable EKG and EEG monitoring electrode which will reduce the resistance of skin or scalp to a satisfactory level and avoids the safety problems incurred with the known electrodes.

It is an object of the present invention to provide a novel type of a disposable EKG and EEG electrode. It is another object of the present invention to provide an electrically conductive composition useful for a disposable EKG or EEG electrode.

BRIEF DESCRIPTION OF THE INVENTION.

The invention relates to a disposable electrode for providing electrical contact with a patient's scalp or skin during routine EEG or EKG tests as well as EEG during full sleeping period in order to record electrical brain or skin waves, which comprises an electrically conductive composition having a volume resistivity in the range of between 1000 to 1500 ohms, acting also as an adhesive to the skin or the scalp by its remoistable property, said composition comprising:

- a partially hydrolysed polyvinyl alcohol;
- a highly hygroscopic salt selected from an alkali metal including ammonium salt, or organic chloride salt;
- a highly electrolytic salt, such as sodium chloride and potassium chloride;
- a metal powder selected from aluminium, bronze and silver.

It was found that by a selection of these constituents in the composition, a proper balance is achieved between the conductivity of the electrode and its property as an adhesive. The performance of the electrodes according to the present invention was found to be the same as those known on the market.

DETAILED DESCRIPTION OF THE INVENTION

The disposable electrode according to the present invention has the advantage that its attachment to the skin or the scalp is only in the order of seconds after remoistening the electrode surfaces for about 1 to 2 minutes and does not require any adhesive or particular 10 solvents to remove the electrode from the skin or the scalp. Also, the electrode does not require any fabric cover, as encountered with the common EKG and EEG electrodes glued to the skin or the scalp.

The main component found according to the present invention, in order to impart the beneficial properties to the composition for the disposable electrode, is a polyvinyl alcohol hydrolysed to an extent of at least 72%. As known, polyvinyl alcohol appears with varying degrees of hydrolysis. It was found that the best results are obtained with a polyvinyl alcohol hydrolysed to an extent of between 82 to 90%, capable of forming highly concentrate solutions in water. As known, the properties of the individual grades are governed to a considerable extent by the molecular weight and the residual acetyl groups. The amount of the hydrolysed polyvinyl alcohol in the composition, may be selected in a broad range of between 20% to 75% by weight, and most preferably between 25% to 45%. The partially hydrolysed polyvinyl alcohol acts also as a binder of the other components, due to its good penetration capacity and good adhesion properties. A defoamer agent may also be incorporated in order to avoid foaming when dissolving the polyvinyl alcohol in water, a preferred one being a blend of parafinic oil and non-ionic emulsifiers.

The hygroscopic salt may be selected from any common salt possessing this property, such as magnesium chloride and particularly in its hydrated form, calcium chloride, aluminium chloride or any mixture thereof, as well as organic salts, such as alkali citrates or acetates, etc. The most preferred salt is magnesium chloride in its hydrated forms. The hygroscopicity of the salt, assists to maintain the water in the final composition and also does regulate its release. The amount of this component should be in the range of between 3% to 35% by weight and most preferably between 5% to 25%.

The incorporation of a strong electrolyte, such as sodium chloride or potassium chloride in an amount of between 1% to 5% by weight,is lowering the impedance of the electrode, which also has a beneficial effect on its operation. The electrically conductive material may be added; this material generally comes in a powder form, most preferably having a particle size in the range of between 8 to 20 microns. In particular, the following metals are most preferred: aluminium, bronze and silver.

The amount of this component may be selected in the range of between 1% to 10% by weight.

In addition to the easy removal of the electrode from the scalp or the skin, the disposable electrode according to the present invention has an advantage that it maintains a desirable low impedance value, even after a period of six hours bonded on the skin or the scalp and thus will minimize motion artifacts or electrical noise, without requiring any other common reagents generally used for this purpose, such as gels.

According to one embodiment, the electrode according to the present invention is connected with carbon fibre conducting leads which will provide stable baselines. This is most desirable since with a metallic wire the electrode will generate signals with an unstable base-line, due to electrons flow between the conducting wire and the metal element dispersed in the electrode matrix. Of course, one may also conceive to made the electrode with a Back-up, made from a plastic material, such as ABS coated with Ag/AgCl, to be connected to the instruments by a conductive material.

The incorporation in the electrode composition of a thixotropic agent was found to prevent settling of the metal powder, improves the flow as well as tackiness of the composition and of the electrode. Typical examples of such thixotropic agents are fumed silica oxide, precipitated silica and bentonite.

The signal quality produced by an electrode, as well as its adhesion on skin or on scalp were found to be the best after a short drying, in the order of 10 to 15 days after casting the composition in the mold, this period may also be significantly decreased by carrying out said drying at an elevated temperature.

The electrode configuration is not critical and may be varied as known in the art,but the cylindrical electrodes having a diameter in the range of 4 to 10 mm, manufactured in a single mold, were found to produce the best signals in their use.

While the invention will be hereafter described in the following Examples in connection with certain preferred embodiments, it is not intended to limit the invention only to these particular embodiments. On the contrary, it is intended to cover all alternatives, modifications and equivalents as may be included within the scope of the invention as covered by the appended claims. Thus, the following Examples which include preferred embodiments serve only to illustrate the practice of this invention, it being understood that the particular shown are by way of example and for purposes of illustrative discussion of preferred embodiments of the present invention. Thus, a person skilled in the art after reading the present specification, with be in a position to insert slight modifications but without being outside the scope of the invention.

In the following Examples the amounts are expressed as weight units (or parts) unless otherwise stated.

EXAMPLE 1

The following compounds were introduced into a vessel:

100 parts water;

25 parts of magnesium chloride hexahydrate;

5 parts of sodium chloride, and 0.3 parts of a blend of non-ionic emulsifier (as produced by Munzing Chemie GmbH, Trade Mark AGITAN 305)

The resulting solution was homogenized by stirring and then an amount of 60 parts of hydrolysed (83%) polyvinyl alcohol (produced by Hoechst "Mowiol 3-83", Trade Mark). The mixture was gradually heated up to a temperature of about 90° C., until all the polyvinyl alcohol was dissolved. 8 parts of aluminium powder having a size of about 15 microns (produced by Alcan, France) was added to the resulting mixture, followed by 4 parts of fumed silicon dioxide produced by Cabot Corp., as a thixotropic agent.

The resulting mixture was cast into a mold containing electrical carbon wires. The water present was evaporated by heating to about 70° C., until reaching a content of about 65% to 70% of the original one, the volume resistivity of the composition being 1250 ohms.

The performance of the electrode produced, was tested on the scalp of a person, and the EEG signals were found to be substantially the same as with a standard electrode.

EXAMPLE 2

The following compounds were introduced into a vessel:

51.3 parts water and 11.5 parts of magnesium chloride hexahydrate;

The resulted solution was homogenized by stirring and then an amount of 30.8 parts of hydrolysed (85%) polyvinyl alcohol (produced by Hoechst "Mowiol 3-85 " Trade Mark) was added. The mixture was gradually heated up to a temperature of about 80° C., until all the polyvinyl alcohol was dissolved. 4.3 parts of aluminium powder (the same as in Example 1) was added to the resulting mixture, followed by 2.1 parts of fumed silicon dioxide as a thixotropic agent (produced by Cabot Corp.).

The resulted mixture was cast into a mold containing electrical carbon lead wires. The water present was evaporated by heating to about 70° C., until reaching a content of about 70% of the original one.

The volume resistivity of the composition was 1195 ohms. The performance of the electrode produced was tested on the scalp of a person and the EEG signals were found to be substantially the same as with a standard electrode.

EXAMPLE 3

The following compounds were introduced into a vessel:

100 parts of water;

21 parts of magnesium chloride hexahydrate, and 6 parts of sodium chloride.

The resulting solution was homogenized by stirring and then an amount of 60 parts of hydrolysed polyvinyl alcohol was added. The mixture was gradually heated up to a temperature of about 90° C. until all the polyvinyl alcohol was dissolved.

The mixture obtained was cast into a cylinder mold made from a plastic material (ABS) coated with silver-silver chloride. The water present was evaporated by heating to about 50° C.–60° C., until reaching a content of about 55–60% of the original one.

The volume resistivity of the composition was 1200 ohms. The performance of the electrode produced was tested on the scalp of a person and the EEG signals were found to be substantially the same as with a standard commercial electrode.

I claim:

1. A disposable electrode for providing electrical contact with a patient's skin or scalp during sleeping, in order to record electrical waves or brain waves, which comprises an electrically conductive composition having a volume resistivity in the range of between 1000 to 1500 ohms, said composition acting also as an adhesive to the skin or scalp by its remoistable property and comprising:

a polyvinyl alcohol hydrolysed to an extent of above 72% and present in an amount between 20% and 75% by weight of the composition;

a highly hygroscopic salt selected from the group consisting of magnesium chloride, calcium chloride, aluminum chloride, an alkali metal citrates, an alkali metal acetate and mixtures thereof; said hygroscopic salt being present in an amount between 3% and 35% by weight of the composition;

a highly electrolytic, alkali metal salt selected from the group consisting of sodium chloride and potassium chloride, said electrolyte alkali metal salt being present in an amount between 1% and 5% by weight of the composition; and a metal powder selected from the group consisting of aluminum, bronze and silver, said metal powder being present in an amount between 1% and 10% by weight of the composition.

2. The disposable electrode according to claim 1, wherein said polyvinyl alcohol is hydrolysed to an extent of between 80% to 90%.

3. The disposable electrode according to claim 1, wherein the amount of the hydrolysed polyvinyl alcohol in said composition, is in the range of between 20% to 75% by weight.

4. The disposable electrode according to claim 1, wherein said highly hygroscopic salt is an organic salt selected from the group consisting of an alkali metal citrate or acetate.

5. The disposable electrode according to claim 1, wherein said highly hygroscopic salt is selected from the group consisting of a hydrated magnesium chloride, calcium chloride, aluminum chloride and any mixture thereof.

6. The disposable electrode according to claim 1 wherein said electrode is connected with carbon fibres conducting leads.

7. The disposable electrode according to claim 1, wherein said composition contains a thixotropic agent which prevents the settling of the metal powder thus controlling the flow properties of the conductive composition and improving the tackiness of the composition.

8. The disposable electrode according to claim 7, wherein said thixotropic agent is selected from the group consisting of fumed silica oxide, precipitated silica oxide and bentonite.

9. The disposable electrode according to claim 1, wherein an antifoaming compound is added.

10. The disposable electrode according to claim 9, wherein said antifoaming compound is selected from a blend of paraffin oil and non-ionic emulsifiers.

* * * * *